United States Patent [19]

Eek

[11] Patent Number: 5,670,524
[45] Date of Patent: Sep. 23, 1997

[54] METHODS AND COMPOSITIONS FOR THE TREATMENT OF PAIN UTILIZING ROPIVACAINE

[75] Inventor: Arne Torsten Eek, Trosa, Sweden

[73] Assignee: Astra AB, Sweden

[21] Appl. No.: 256,319

[22] PCT Filed: May 26, 1994

[86] PCT No.: PCT/SE94/00496

§ 371 Date: Jun. 28, 1994

§ 102(e) Date: Jun. 28, 1994

[87] PCT Pub. No.: WO95/00148

PCT Pub. Date: Jan. 5, 1995

[30] Foreign Application Priority Data

Jun. 28, 1993 [SE] Sweden ................... 9302218

[51] Int. Cl.$^6$ .............................. A61K 31/445
[52] U.S. Cl. ..................................... 514/330
[58] Field of Search ............................. 514/330

[56] References Cited

FOREIGN PATENT DOCUMENTS

WO85/00599  2/1985  WIPO.

OTHER PUBLICATIONS

"Drugs of the Future", vol. 14, No. 8, pp. 767–771 1989.
Concepcion et al., Anethesia and Analgesia, 70(1), pp. 80–85 (abstract only) 1990.
Wahedi et al. Regional–Anaesthesie, 13(3), pp. 57–65 (abstract only) 1990.
Wahedi et al., Regional–Anaesthesie, 13(3), pp. 66–72.(abstract only) 1990.
Zaric et al., Anesthesia and Analgesia, 72(4), pp. 509–515 (abstract only) 1991.
Katz et al., Biopharmaceutics & Drug Disposition, 14(7), pp. 579–588 1993.
Wood et al., Anesthesia and Analgesia, 76(6), pp. 1274–1278 1993.
Chem. Abst. No. 117:239834, Broberg et al. 1992.
Chem. Abst. No. 115:22086, Cederholm et al. 1991.
Chem. Abst. No. 111:90290, Kopacz et al. 1989.
Brockway, M.S. et al., "Comparison of Extradural Ropivacaine and Bupivacaine," *British Journal of Anaesthesia* 66:31–37 (1991).
Concepcion, M. et al., "A New Local Anesthetic, Ropivacaine, Its Epidural Effects in Humans," *Anesth. Analg.* 70:80–85 (1990).
Zaric, D. et al., "Blockade of the abdominal muscles measured by EMG during lumbar epidural analgesia with ropivacaine—a double–blind study," *Acta Anaesthesiol* 37:274–280 (1993).

*Primary Examiner*—Raymond Henley, III
*Attorney, Agent, or Firm*—Michael A. Sanzo; Vinson & Elkins

[57] ABSTRACT

Use of a pharmaceutically acceptable salt of ropivacaine for the manufacture of a pharmaceutical preparation with sensoric block and minimal motor blockade.

10 Claims, No Drawings

METHODS AND COMPOSITIONS FOR THE TREATMENT OF PAIN UTILIZING ROPIVACAINE

This application is a 371 of PCT/SE94/00469 filed May 26, 1994.

1. Field of the Invention

The present invention is related to the use of a low concentration of a pharmaceutically acceptable salt of ropivacaine in the manufacture of pharmaceutical preparations for pain relief post operatively and in labour.

2. Background of the Invention

Post operative pain relief is still a problem within modern surgery. According to a newly published study about 70% of all patients treated surgically felt moderate to severe pain after the surgical treatment.

The need for qualified pain relief is greatest during the first 24 hours after the surgical treatment. The traditional method to treat the patients is to give narcotics intramuscularly or intravenously. Such treatment is often insufficient as narcotic analgetics have many negative effects. One disadvantage is depression of the breathing, which may occur even after treatment. This means that the patient must be intensively looked after by specialists.

A patient, who has been treated with morphine is tired, apathetic and is often feeling sick. The patient thus has no interest in things around him. It is thus difficult to take care of the patient and make him participate in respiratory exercises and prophylaxis for thromboses.

One method is administration epidurally, by infusion or intermittent injections of local anaesthetics. Such treatments can only be carried out on patients with epidural catheters being taken care of at an intensive care or post surgical unit by specially trained persons.

There has been a long felt need at ward level to be able to give a greater group of patients qualified pain relief by epidural infusion of e.g. local anaesthetics instead of opiates.

Normally, with local anaesthetics a good blockade of the pain is obtained. The drawback is the motor blockade in the legs, which is disturbing to the patients, who wants to give up the pain relief treatment in advance. Among other effects the motor blockade means that the patient cannot leave his bed without assistance as the legs will not bear.

Outline of the invention

According to the present invention it has surprisingly been found that the local anaesthetic agent ropivacaine, described e.g. in WO/85/00599, in form of its hydrochloride can be given to the patient in a dosage which gives pain relief with minimal effect on motor function. This is at a dosage of lower than 0.5% by weight, especially from 0.01% to 0.45% by weight. Such low dosages are normally considered to be ineffective. The normal dosage is from 0.5-2% by weight.

The local anaesthetic compound used according to the invention is in the form of its pharmaceutically acceptable salts. It is especially preferred to use ropivacaine hydrochloride.

The local anaesthetic is incorporated into a solution.

The local anaesthetic composition contains less than 0.5% by weight of the local anaesthetic compound, preferably from 0.01 up to 0.45% by weight, especially preferred 0.1-0.3% by weight.

Pharmaceutical Preparations

EXAMPLES 1–3

Solution 5 mg/ml, 3 mg/ml, 2 mg/ml

|  | Examples | | |
| --- | --- | --- | --- |
|  | 1 | 2 | 3 |
| Ropivacaine hydrochloride monohydrate | 0.53 kg | 0.32 kg | 0.21 kg |
| Sodium hydroxide 2M to pH 5.0–6.0 |  |  |  |
| Purified water qs ad | 100 kg | 100 kg | 100 kg |

Ropivacaine is dissolved in the water. Sodium hydroxide is added to pH 5.0–6.0. The resulting solution is autoclaved.

The best mode of carrying out the invention known at present is to use the preparations according to Example 3.

Biological test

A double blind study of sensory and motor blockade with 0.1%, 0.2%, 0.3% ropivacaine and 0.25% bupivacaine during continuous epidural infusion in healthy male volunteers.

Background

The aim of the study was to find a low concentration of ropivacaine giving a sufficient sensory block but as little or no motor block at all during continuous epidural infusion. This study is a first step towards finding a low concentration of ropivacaine which later will be used for treatment of post operative pain in patients. 37 volunteers participated in the study. They were divided into 5 treatment groups, receiving either 0.1%, 0.2% or 0.3% ropivacaine or 0.25% bupivacaine. There was also a control group receiving 0.9% saline. All solutions were first given as a bolus dose of 10 ml, followed by a continuous epidural infusion at a rate of 10 ml/hour for 21 hours. During the infusion both motor and sensory blockade was tested using different methods. The postural stability of the volunteers was also evaluated.

Preliminary results

Group 1. No motor and sensory block was achieved in the volunteers receiving saline.

Group 2. Bupivacaine 0.25% gave a good segmental spread (from the lower part of the abdomen to the lower part of the extremities) of sensoric block during the infusion. All of the volunteers had a high degree of motor block and 75% (6/8) could not stand up at any occasion during the infusion.

Group 3. Ropivacaine 0.3% gave an equal duration of sensory blockade compared to bupivacaine 0.25%. The upper segmental spread of sensoric block was somewhat higher than for bupivacaine. The lower segmental spread of sensoric block was, after 10 hours of continuous infusion, shifted up to just below the knees compared to bupivacaine and at the end of infusion was found above the knees. The motorblock was somewhat less profound compared to bupivacaine. 5 out of 7 volunteers could not stand at any occasion during the infusion to perform the postural stability tests.

Group 4. Ropivacaine 0.2% gave an equal sensory block compared to bupivacaine 0.25% in the lower part of the abdomen, but showed a less sensory block around the ankles. After 10 hours of continuous infusion the sensory block was less than for both ropivacaine 0.3% and bupivacaine. The motor block was less profound compared to the 0.3% ropivacaine as well as to the 0.25% bupivacaine solution. 25% (2/8) of the volunteers could not at any occasion stand up whereas the rest of the volunteers (6/8) could at some point during the infusion make some of the postural tests.

Group 5. Ropivacaine 0.1% gave, during the first 5 hours of the infusion, a more narrow spread of the sensory block compared to the 0.2% ropivacaine solution. Normal sensation returned after 8 hours of the epidural infusion.

No serious or unexpected adverse events could be noted in any of the test groups.

It was found that bupivacaine gives 75% higher motor blockade than ropivacaine, which only gives 25% at comparable dosage levels.

At the dosages 0.3% and 0.2% ropivacaine gives about the same motor blockade. At the dosage 0.1% it is less.

Conclusion

From the unique effect of ropivacaine the conclusion can be drawn that said compound is especially useful for administering at low dosage to patients in the need of post surgical and labour pain treatment, with good balance between sufficient sensoric block and a desirable minimal degree of motor block.

I claim:

1. A method for treating a human experiencing pain, said method comprising: administering to said human a composition comprising a pharmaceutically acceptable salt of ropivacaine, wherein said ropivacaine is present in said composition at a concentration of less than 0.25% by weight.

2. The method of claim 1, wherein said composition is administered at a site permitting direct interaction between said ropivacaine and nerves in the spinal column of said human.

3. The method of claim 1, wherein said composition is administered epidurally.

4. The method of any one of claims 1-3, wherein said pharmaceutically acceptable salt of ropivacaine is ropivacaine hydrochloride.

5. The method of any one of claims 1-3, wherein said composition is administered by continuous infusion.

6. The method of claim 5, wherein said continuous infusion is at a flow rate of about 10 ml per hour.

7. The method of any one of claims 1-3, wherein said composition is administered for post-surgical pain.

8. The method of any one of claims 1-3, wherein said composition is administered for labor pain.

9. A pharmaceutical composition for use in acute pain management with minimal motor blockade, comprising a pharmaceutically acceptable salt of ropivacaine at a concentration lower than 0.25% by weight.

10. The pharmaceutical composition of claim 9, wherein said pharmaceutically acceptable salt of ropivacaine is ropivacaine hydrochloride.

* * * * *

(12) EX PARTE REEXAMINATION CERTIFICATE (10499th)

United States Patent
Eek

(10) Number: US 5,670,524 C1
(45) Certificate Issued: Feb. 10, 2015

(54) METHOD AND COMPOSITIONS FOR THE TREATMENT OF PAIN UTILIZING ROPIVACAINE

(75) Inventor: Arne Torsten Eek, Trosa (SE)

(73) Assignee: Astrazeneca UK Limited, London (GB)

Reexamination Request:
No. 90/011,068, Jul. 16, 2010

Reexamination Certificate for:
| | |
|---|---|
| Patent No.: | 5,670,524 |
| Issued: | Sep. 23, 1997 |
| Appl. No.: | 08/256,319 |
| PCT Filed: | May 26, 1994 |
| PCT No.: | PCT/SE94/00496 |
| § 371 (c)(1), (2), (4) Date: | Jun. 28, 1994 |
| PCT Pub. No.: | WO95/00148 |
| PCT Pub. Date: | Jan. 5, 1995 |

(30) Foreign Application Priority Data

Jun. 28, 1993 (SE) .................................... 9302218

(51) Int. Cl.
*C07D 211/60* (2006.01)
*A61K 31/44* (2006.01)
*A61K 31/445* (2006.01)
*A61P 23/02* (2006.01)
*A61P 25/04* (2006.01)
*A61P 29/00* (2006.01)

(52) U.S. Cl.
CPC .................................. *C07D 211/60* (2013.01)
USPC ......................................................... 514/330

(58) Field of Classification Search
None
See application file for complete search history.

(56) References Cited

To view the complete listing of prior art documents cited during the proceeding for Reexamination Control Number 90/011,068, please refer to the USPTO's public Patent Application Information Retrieval (PAIR) system under the Display References tab.

*Primary Examiner* — Bruce Campell

(57) ABSTRACT

Use of a pharmaceutically acceptable salt of ropivacaine for the manufacture of a pharmaceutical preparation with sensoric block and minimal motor blockade.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-10 are cancelled.

\* \* \* \* \*